United States Patent [19]

Taguchi et al.

[11] Patent Number: 4,882,423

[45] Date of Patent: Nov. 21, 1989

[54] SUBSTANCE-CONJUGATED COMPLEMENT COMPONENT C1Q

[75] Inventors: Fumiaki Taguchi, 14-1, Yokodai 5-chome, Sagamihara-shi, Kanagawa-ken; Isamu Mitsui, Yokohama; Kinichi Hara, Yokohama; Masaro Hayashi, Yokohama; Kunio Ezawa, Tokyo; Kenichi Fukunaga, Tokyo; Jun Kuranari, Tokyo; Masatoshi Sonoda, Tokyo; Yasuo Satou, Tokyo, all of Japan

[73] Assignees: Calpis Food Industry; Fumiaki Taguchi, both of Japan

[21] Appl. No.: 32,025

[22] Filed: Mar. 30, 1987

Related U.S. Application Data

[63] Continuation-in-part of Ser. No. 779,671, Sep. 24, 1985, abandoned.

[30] Foreign Application Priority Data

| Oct. 2, 1984 | [JP] | Japan | 59-205686 |
| Oct. 25, 1984 | [JP] | Japan | 59-223049 |
| May 17, 1985 | [JP] | Japan | 60-103898 |
| Jul. 24, 1985 | [JP] | Japan | 60-162012 |
| Jul. 29, 1985 | [JP] | Japan | 60-166004 |
| Mar. 31, 1986 | [JP] | Japan | 61-70936 |
| Mar. 31, 1986 | [JP] | Japan | 61-70937 |
| Mar. 31, 1986 | [JP] | Japan | 61-70938 |

[51] Int. Cl.$^4$ .............................................. C07K 15/00
[52] U.S. Cl. .................................. 530/380; 435/4; 435/14; 435/21; 435/26; 435/28; 435/7; 514/2; 514/3; 514/6; 530/350; 530/404; 530/408
[58] Field of Search ............... 530/404, 408, 350, 380; 435/4, 7, 14, 21, 26, 28; 514/2, 3, 6

[56] References Cited

U.S. PATENT DOCUMENTS 4,184,847  1/1980  Hallgren et al. .................... 436/800
4,595,654  6/1986  Reckel et al. ....................... 530/380

OTHER PUBLICATIONS

Smith et al-J. of Immunol. Methods vol. 67 (1984) pp. 167–172.
Alcolea et al.-Mol. Immunol. vol. 23(1) (1986) pp. 39–44.
Alcolea et al.-Chem. Abst. vol. 104 (1986) p. 86773e.
Reid et al.—Chem. Abst. vol. 101 (1984) p. 53053e.
Nishioka et al.—Chem. Abst. vol. 97 (1982) p. 196,644h.
Bing et al.—Chem. Abst. vol. 97 (1982) p. 53755j.
Ingham et al.—Chem. Abst. vol. 98 (1983) p. 177,328n.

*Primary Examiner*—Sam Rosen
*Attorney, Agent, or Firm*—Darby & Darby

[57] ABSTRACT

A substance-conjugated complement component C1q is provided. A substance such as signal emitting substances or cell function regulating substances is conjugated via a sulfur atom to at least one site of the component. The site is not involved in binding immunoglobulins. A marker-labelled complement component C1q is used for measuring a complement-binding antibody, an antigen, a neutralizing antibody or a substance produced internally of and at the surface of a cell or a microorganism by measuring the marker.

31 Claims, 1 Drawing Sheet

SUBSTANCE-CONJUGATED COMPLEMENT COMPONENT C1Q

CROSS-REFERENCE TO RELATED APPLICATION

This application is a continuation-in-part application of application Ser. No. 779,671 filed Sept. 24, 1985, now abandoned.

BACKGROUND OF THE INVENTION

1. Field of the Invention;

This invention relates to a substance-conjugated complement component C1q and a process for preparing the same, and a method for measurement, using the substance-conjugated complement component C1q. More particularly, it relates to a complement component C1q conjugated with various substances including markers and cell function regulating substances and a process for preparing the same, and also to a process for measurement, using such a substance-conjugated complement component C1q.

2. Related Art Statement;

It has hitherto been known to utilize the complement fixation reaction for the measurement or determination of antibodies in blood serum and antigens, such as microorganisms, phisiologically active substances and chemicals. This known method makes use of the serial reactions wherein complement components C1 to C9 are bound successively to an antibody specifically bound to an antigen. In detail, this known method comprises the step of adding an excess amount of complement components to the formed antigen-antibody complex, the step of determining an amount of residual complement components through the hemolysis, and the step of determining the amount of fixed complement components from the degree of hemolysis. The quantity of the antigen or antibody is then estimated from the results of the amount of the fixed complement components. In the hemolysis, complement components act on the sensitized erythrocytes including sheep red blood cells and anti-sheep red blood cell antisera so that the complement components may be determined while using the hemolysis of the sheep red blood cells as the index. However, practical determination operation of the hemolysis is extremely complex and needs high level skill and knowledge. In addition, this known method has a relatively low sensitivity and requires two days for the determination operation.

Various methods have been proposed to overcome the aforementioned disadvantages of the known method as described in the preceding paragraph. For example, Japanese Patent Laid-Open Publication No. 43498/1980 discloses one of such methods. In the method proposed by the antecedent Publication referred to above, an antibody which binds, as an antigen, a complement component being bound to another antibody is labelled with an enzyme, and the amount of the thus labelled antibody is determined by the enzymatic activity thereof. This method is, therefore, one of the so-called enzyme-labelled antibody techniques. However, this method involves two step reactions, since a labelled antibody which binds, as an antigen, a complement component must be used. Accordingly, rinsing operations are required after each of the reactions, leading to increase in labor and time. In fact, this determination method costs much time as several hours.

On the other hand, a method of determining a neutralizing antibody has been made known, for example, by Takashi Kitamura, "Tissue Culture Technology for Inspection of Virus", published by KINDAI SHUPPAN (1980), page 246. When an antibody against poliovirus, for instance, is determined by this method, cultivated cells originated from human being, a monkey or an ape are first inoculated with the poliovirus. (Meanwhile, the poliovirus does never grow if it is inoculated into cells originated from the sources other than human being, a monkey or an ape.) The cells inoculated with the poliovirus collapse and are deseased as the result of cytopathogenesis due to propagation of the virus. However, the reaction product of a neutralizing antibody and the virus, (the infectiousness of virus being neutralized by the neutralizing antibody), can not propagate even if it is inoculated upon a cell originated from human being or monkey so that the cell is kept to have normal form and functions. Making use of this principle, a specific virus is reacted with blood serum and then the titre of the neutralizing antibody is determined by inspecting the presence or absence, and the degree if present, of plaque and CPE (cytopathogenic effect).

However, when the poliovirus is determined by the method described in the preceding paragraph, the poliovirus must be cultivated for about 7 days in a normal test in addition to the fact that the inspection and judgement of the result should be made by a skilled person rather than being easily conducted by a person having ordinary or middle level skill. For this reason, an order of test for the determination of neutralizing antibody is not accepted even by a large scale inspection center at the present day.

On the other hand, as a method for determining antigens or antibodies in a simpler way, there has been known in the art a method wherein properties of complement component C1q binding an antigen-antibody complex is utilized. (Simpson et al., "Jounal of Immunological Methods", Vol. 67, 167 to 172 (1984).) In this known method, glutalaldehyde or periodic acid is conjugated to the complement component C1q as a cross-linker, and peroxidase (enzyme) is conjugated via said cross-linker to the complement component C1q as a marker. Marchalonis J. J., "Biochemical Journal", Vol. 113, pp229 to 305 (1969) discloses a method in which radioactive iodine is conjugated to the complement component C1q through the chloramine T method as a marker. However, in these known methods, an enzyme or radioactive iodine is coupled with each of the complement component C1q molecules via an amino group present on the molecule generally and at random, resulting in entire modification of the molecule since the very site of each molecule having inherent properties capable of binding to an immunocomplex has been chemically modified by said cross-linker or coupler. Accordingly, the binding activity of such a marker-labelled complement component C1q for binding to an antigen-antibody complex is seriously lowered to a level not to adapt for quantitative measurement as a reagent. Moreover, a false-positive reaction takes place frequently by the latent presence of said cross-linker in the marker-labelled complement component C1q to make it impossible to continue the determination operations. It has, thus, been impossible to provide a reliable determination method for determining an antigen or antibody in a precise and reproducible manner by the use of the complement component C1q.

OBJECTS AND SUMMARY OF THE INVENTION

It is, therefore, a primary object of this invention to provide a complement component C1q which is conjugated with a variety of substances, such as markers or cell function regulating substances, while preserving its inherent binding capacity for binding with an immunocomplex without any detraction, and a process for preparing such a complement component C1q, and to provide a determination method in which such a complement component C1q is used in a substance-conjugated condition.

Another object of this invention is to provide a complement component C1q which is conjugated with a variety of substances to be conveniently used as a determination or detection reagent for determining or detecting a specific antigen present in a body fluid or held or bound to a cell or body tissue or for determining or detecting the corresponding antibody for the specific antigen, a modified immunoglobulin or immunocomplex, and a process for preparing such a complement component C1q, and to provide a determination method in which such a complement component C1q is used in a substance-conjugated condition.

A further object of this invention is to provide a complement component C1q which is conjugated with a variety of substances to be conveniently used as a curing agent or medicine for regulating physiological function of a variety of cells which have cell surface structures identified by specific antibodies or which can capture specific immunocomplexes or complements, and a process for preparing such a complement component C1q, and to provide a determination method in which such a complement component C1q is used in a substance-conjugated condition.

A still further object of this invention is to provide a determination method utilizing a complement component C1q, which is simple and easy in determination operation and can be conducted for a short operation time even by an unskilled person.

Yet a further object of this invention is to provide a determination method utilizing a complement component C1q, which has high sensitivity to give reproducible result of determination.

The above and other objects of this invention will be apparent from the following detailed description thereof.

According to the present invention, there is provided a complement component C1q wherein a substance is conjugated via a sulfur atom to at least one site of said component, said site being not involved in binding immunoglobulins.

Also provided in accordance with this invention is a process for preparing a substance-conjugated complement component C1q, comprising the steps of:

(a) adding a reducing agent to a complement component C1q to cleave at least one S—S bond present at a site not involved in binding immunoglobulins thereby to obtain a reduced complement component C1q having at least one exposed —SH group; and (b) conjugating a substance to said complement component C1q via said exposed —SH group.

Further provided in accordance with the invention is a method for measurement by the use of a complement component C1q comprising reacting a maker-labelled complement component C1q with a material to be measured, said complement component C1q being conjugated with the marker at at least one site not involved in binding immunoglobulins, thereby to obtain a reaction material having said marker, and measuring said marker.

BRIEF DESCRIPTION OF THE DRAWING

The single FIGURE, FIG. 1, of the appended drawing is a graph showing the change in neutralizing antibody titer of an anti-HSV positive human serum in Example 15, one of the examples of the invention.

DESCRIPTION OF THE INVENTION

Figure 1:
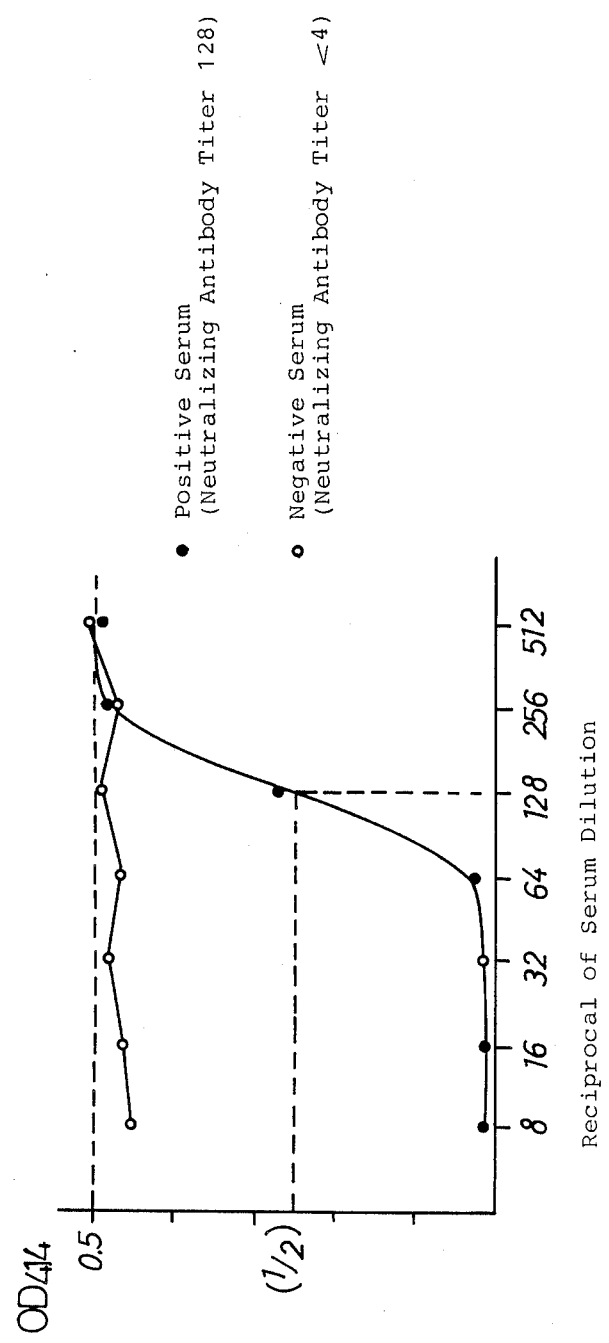

The present invention will now be decribed in detail.

In general, after an antigen is bound to an antibody, a complement is bound to the antibody already bound with the antigen to destruct the antigen. The complement includes complement components C1q, C1s, C1r, C2a, C2b, C3a, C3b, C4b, C5b, C6, C7, C8 and C9, and each one of these complement components binds to a specific antibody pertinently depending on the specific immunological reaction or allergy rection. These complement components bind in a fixed order such that the component C1q binds to the antigen at a first place, followed by binding of C1s and C1r to C1q, and then the other complement components bind serially.

After eager investigations with the estimation that a substance-conjugated complement component having a utility when used as a determination reagent or a curing agent might be prepared by conjugating a variety of substances to the complement component C1q, which is the component coupled with an antigen-antibody complex at the first place, such that the subsequent binding between the immunoglobulins acting as an antibody and the component C1q is not hindered, we have succeeded to allow a variety of substances to conjugate at sites of the complement component C1q other than the sites at which the immunoglobulins are to be bound.

In detail, we have given attention to the presence of nine S—S bonds located at the sites of the polypeptide molecule of the complement component C1q, the S—S bonds locating at the sites remote enough for affecting the site having the binding capability for the immunoglobulins and being formed by the fourth cysteine residues from the N-terminals of the A, B and C chains of the polypeptide constituting the complement component C1q so that they are apt to be attacked by a reducing agent and apt to conjugate with a substance readily.

In view of the presence of such S—S bonds, we have contemplated to cleave these S—S bonds by the action of a reducing agent to expose at leat one S—H group in a step (a) of the process provided by the present invention.

The reducing agents which may be conveniently used in this step (a) include those used conventionally, the examples being sulfur-containing compounds, such as mercaptoethylamine, dithiothreitol, 2-mercaptoethanol, cysteine and glutathione.

The reducing step is carried out under the condition that the complement component C1q is not modified. Preferably, reducing may be effected by dissolving the complement component C1q in a buffer solution in which it exists stably and then it is attacked by a reducing agent. Examples of the buffer solution used for this purpose include a tris buffered saline containing 10% of sucrose, 1 mol of sodium chloride and 5 mM (millimols) of sodium ethylenediamine tetra-acetate, and a phosphate buffered saline (PBS). The reducing reaction is carried out, generally, at about $-2°$ C. to $45°$ C. for about 30 seconds to 24 hours, the reaction temperature and time being changed depending on the specific reducing agent used.

It is desirous that the thus reduced complement component C1q be stored in a buffer solution to be used in the subsequent step (b) after removing the excess reducing agent by means of a conventional method, such as dialysis, salting-out process or gel filtration.

The complement component C1q utilized in the present invention is a glycoprotein contained in the blood serum of animal, and has nature for binding firmly to the immunoglobulins when the immunoglobulins contained similarly in the blood serum and acting as an antibody react specifically with the corresponding antigen. The complement component C1q used in the invention may be isolated from various aminals including sheep, rabbit, guinea pig, cattle, horse, dog, mouse and human being, and the fraction enriched in the C1q component may be picked up in accordance with a conventional purifying operation. (In this connection, reference should be made to "Operations in Immunological Experiment B", published by the Japanese Immunological Society, pp 1376 to 1380 (1974), if necessary.)

In the process of the invention, a variety of substances is conjugated via the exposed SH group of the reduced complement component C1q at the subsequent step (b). The substances to be used in the step (b) and to be conjugated with the complement component C1q via the exposed SH group include signal emitting substances, such as enzyme substrates, dyestuffs or pigments, magnetizable substances, donors or acceptors for electron transference, radioactive materials, metal compounds and metal compositions, which emit signals detectable by the sensory organs or external instruments, enzymes or coenzymes which may be modified to emit detectable signals or agglutinating substances which get together, thereby to be readily detected; cell function regulating substances, for example, certain enzymes which act on the counter-substances conjugated to the complement component C1q to provide the latter with any functions; and substances, such as high polymer materials, which capture or fix the counter-substances conjugated to the complement component C1q.

More specifically, examples of the enzyme substrate are o-nitrophenyl-$\beta$-D-galactopyranoside and 3-hydroxysteroid; and dye stuffs or pigments include hemoglobin, the redox dyestuffs, such as methylene Blue, and fluorescent dyestuffs, such as fluorescein isothiocyanate. Examples of the magnetizable substance are organic irons, such s carbonic iron, and microcapsules containing iron, and complexes of iron with proteins may also be used. The donors and acceptors for electron transference include a wide variety of substances which take part in the electron transference, and chlorophyll which may be energized to take part in the electron transference is included in this group of substance and preferably used in the invention. Examples of the radioactive substances are $^{124}$I-labelled albumin, p-chloro($^{203}$Hg)mercuribenzoic acid, N-ethyl(2,3-$^{14}$C)maleimide and iode(1-$^{14}$C)acetamide.

The metal compounds and compositions, other than the corbonic iron referred to hereinabove, which may be used in the invention include gold colloid and iron-containing microbeads.

Examples of the enzymes are peroxidase, alkaline phosphatase, galactosidase and alcohol dehydrogenase; wheras examples of the coenzymes are nicotinamide adenine dinucleotide, nicotinamide adenine dinucleotide phosphate, flavin adenine dinucleotide and flavin adenine dinucleotide phosphate.

Example of the agglutinating substances are agglutinative fine particles such as latexes or microbeads; and other complement components C1q, i.e. complement components C1q to be conjugated with the exposed SH group of the reduced complement component C1q. These substances per se form agglutinate masses, which may be conjugated with the reduced complement component C1q. The other examples of the agglutinating substances include a combination of antibodies such as IgG or IgM and antigens corresponding to the respective antibodies, a combination of lectins such as peanut lectin or wheat embryo lectin and materials having the corresponding saccharide structures, a combination of biotin and avidin and a combination of protein and IgM. In a case where these combinations are used, one material forming the combination is conjugated with the reduced complement component C1q and then the other material forming the combination is added to form agglutinate masses. If the agglutinating substances are used as a marker, the marker is easily detected by turbidity.

A variety of substances may be included in the cell function regulating substance and conveniently used in the invention, examples being surface active agents; antibiotics having activities to vital membranes, such as amphotericin B, and antibiotics affecting the metabolisms of cells, such as actinomycin D; trace essential nutrients or growth factors indispensable for the growth of cells, such as selenium compounds, insulin, transferring and epidermal growth factor; hormones such as corticosteroid; factors, participating in the manifestation of cell function, such as macrophage activation factor; factors participating in the cell division, such as B cell division factor; anticancer agents, scuh as mitomycin C; and toxins such as ricin of toxin of castor bean.

For instance, an enzyme may be utilized as the signal emitting substance while being conjugated to the complement component C1q to act as a marker so that it is used as a determination or detection reagent for determining or detecting a specific antigen present in a body fluid or held by or adhering to a cell or body tissue, or for determining or detecting the corresponding antibody to said antigen, modified immunoglobulin or an immunocomplex.

When an antibiotic is used as the cell function regulating substance while being conjugated to the complement component C1q, the conjugated product may be used as a curing agent for controlling the physiological function of a cell having a cell surface structure which can be identified by a specific antibody or a cell capable of capturing an immunocomplex or a complement.

In the aforementioned step (b) of the process of the invention, a substance having a group which can be conjugated to the exposed -SH group may be directly conjugated to the reduced complement component C1q, or a substance may be conjugated indirectly to the complement component C1q via a second substance having a coupling function, for example, via one or more spacers or cross-linkers. Examples of the substance which may be directly conjugated include activated thiol Sepharose (Trade Name of Pharmacia Fine Chemicals Co.) and p-chloromercuribenzoate. Any substance having a group capable of conjugating to the exposed —SH group of the complement component C1q, such as maleimide residue or —SH group, and also having another group capable of coupling with the substance to be coupled indirectly with the complement component C1q may be used as the coupling agent for such purpose.

The coupling agent or the second substance having a coupling function, of course, varies depending on the substance to be coupled thereby. As an illustrative example, when peroxidase extracted from horseradich is coupled by the N-hydroxysuccineimide ester of N-(4-carboxycyclohexylmethyl)maleimide, both reagents are dissolved in a buffer having a pH value of 6.5 to 7.5 and containing sodium ethylenediamine tetra-acetate to allow them to react with eath other at 30° C. for an hour. The reaction conditions are selected in consideration of the characteristics of a cross-linker used. Other than the N-hydroxysuccineimide ester of N-(4-carboxycyclohexylmethyl)maleimide referred to above, N-hydroxysuccineimide esters of m-maleimide benzoic acid, N-(4-carboxyphenylmethyl)maleimide and maleimide acetic acid may be used as the cross-linker. A peroxidase having therein a maleimide group is produced. The thus produced peroxidase having a maleimide group is mixed with the reduced complement component C1q, and maintained in a buffer held at pH 5.5 to 6.5 and containing sodium ethylenediamine tetra-acetate at 4° C. for 2 hours, whereby a complement component C1q conjugated with peroxidase is obtained.

At the final step, the fraction of the complement component C1q labelled with peroxidase, which serves as a marker, and having the activities originated both from the peroxidase and the complement component C1q may be picked up through the gel filtration As another illustrative example, if an antibody is employed as the agglutinating substance, an antibody having a maleimide group is obtained by the similar procedures under the similar conditions as explained hereinabove with respect to peroxidase extracted from horseradish. When the antibody having the maleimide group is mixed and reacted with the reduced complement component C1q, a complement component C1q conjugated with the antibody is obtained.

As a further illustrative example, if another complement component C1q is employed as the agglutinating substance, the complement component C1q is firstly reduced by the procedures described hereinabove with respect to the step (a). Then, the reduced complement component C1q is put in a buffer solution containing ethylenediamine tetre-acetate and N,N'-para-phenylene dimaleimide at pH 5.5 to 6.5 and is maintained for 20 hours at 4° C., so that conjugated complement components C1q each conjugated via S—S bond to form an agglutinate mass and having maleimide groups are obtained. When the conjugated complement components C1q are mixed and reacted with the reduced complement component C1q, a complement component C1q further conjugated with complement components C1q is obtained.

It is preferred that the step (b) of the process of the invention be carried out in the presence of a buffer for both of the reduced complement component C1q and the substance to be conjugated thereto, and carried out in the presence of a buffer for the coupler or cross-linker in case where such a substance having the coupling or cross-linking function is used.

In the substance-conjugated complement component C1q provided according to this invention, the substance is conjugated at a site or sites having no binding capacity with the immunoglobulins, so that the binding capability to the immunoglobulins inherent to the complement component C1q is kept intact without being hindered by the conjugating substance.

Since the substance-conjugated complement components C1q provided according to this invention are conjugated with various signal emitting substances and cell function regulating substances without blocking the sites at which the immunoglobulins is to be bound, they may be used for various applications including determination or measurement reagents giving the reproducible results or curing medicines in which their inherent capacities for binding with the immunoglobulins are utilized.

The method for the measurement or determination, according to the invention, utilizing the substance-conjugated complement component C1q will now be described. The signal emitting substances, as described hereinbefore, may be used in the measurement method according to the invention. Such a signal emitting substance may be utilized as a marker. In detail, a substance-conjugated complement component C1q having a marker conjugated at a site that is not adapted to bind with the immunoglobulins is prepared, and then the thus prepared marker-labelled complement component C1q is allowed to react with another material to be measured, whereby a reaction product conjugated with the marker is obtained, Subsequently, the labelled marker is qualitatively or quantitatively analysed to measure a variety of antigens, antibodies, neutralizing antibodies, substances produced or appearing in cells or on the surfaces of cells or microorganisms. In this manner, the method of the invention may be applied for comprehensive uses, including various clinical inspections and diagnoses of diseases.

One group or category of the substances which may be measured by the method of the invention includes complement-binding antibodies. By the determination of certain complement-binding antibodies, various diseases of wide-ranging hosts including not only human beings but also animals and plants may be diagnosed and judgement may be made whether the hosts are infected or not, the diseases which may be determined by the method of the invention including infectious diseases caused by microorganisms, such as bacterium, chlamydia and virus, tumor and autoimmune diseases such as systemic lupus erythematodus. Particularly in clinical inspection of such an infectious disease and autoimmune disease, it is a common practice to inspect whether or not a specific antibody uniquely appearing with a certain disease is present in the blood serum. Various measurement or inspection methods are known, and the complement-binding reaction is involed in one of the important inspection methods. Notwithstanding that this complement-binding reaction has a utility when utilized in a method of inspecting a certain specific antibody, the reaction has not been frequently uesd, irrespective of the importance thereof, since it involves cumbersome determination operations and requires extremely high level skill.

Under these circumstances, a considerable contribution in industrial and medical fields is made by the provision of a simple and speedy method based on this principle is developed to give a reproducible measurement or determination value at high sensitivity.

In determination of a complement-binding antibody in accordance with the present invention, an antigen is initially fixed to a solid phase or carrier, and then the fixed antigen is allowed to react with an antibody and with a complement component C1q combined with a marker, followed by removal of unreacted materials and then the marker is quantitatively analysed. Utilizable antigens include viruses and bacteria, such as varicella-zoster virus, measles virus, rubella virus, influenza virus, herpes simplex virus, hepatitis virus, mumps virus and mycoplasma phneumonitis; physiologically active substances such as interferon; and antigens against autoantibodies such as DNA. Initially, such an antigen is fixed to a solid carrier to form a solid phase. Whereupon, the operations, particularly rinsing operations, can be carried out easily as compared with the prior art technology in which a lquid phase must be handled. Any carries may be used as far as the antigen absorbed thereby is not easily released from the solid phase, the examples being synthetic high polymers such as polyvinylchloride and polystyrene, natural high polymers such as filter paper, and cells and tissues. More specifically, a microtiter plate and polystyrene beads may be referred to as illustrative examples. The antigen may be fixed to the solid phase by fixing the same on the surface of the solid carrier through physical absorption of chemical covalent bond and the like. In case where a cell or tissue is used as a solid carrier, the antigen may also be fixed thereto by infection.

Then, the fixed antigen is allowed to react with the specific or corresponding antibody and a complement component C1q combined with a marker. The antibody is the objective substance which is to be measured or inspected by the method of the invention, according to the aspect of the invention discussed just now, and the examples thereof are body fluids, such as blood serum, cerebrospinal fluid and saliva. The blood serum is used most frequently, since it contains the largest quantities of antibodies. The antibodies determined or measured by the method of the invention must bind to the corresponding antigens uniquely or specifically, and must be capable of binding to the complement components. However, almost all of the antibodies produced in living bodies satisfy the aforementioned conditions, and hence they may be measured by the method of the invention.

The reaction of the antigen fixed to the solid phase, the antibody and the complement component C1q conjugated with a marker takes place spontaneously by simply mixing the aforementioned three reactants together to complete the reaction for forming a combined product. While the reaction temperature and reaction time vary depending on the specific antigen or other reactants used, these conditions may be selected properly unless bioactivities are lost.

Since the complex composed of the antigen, the antibody and the marker-labelled complement component C1q is fixed to a solid phase, the unabsorbed complement component C1q and inhibitors for the reaction can be readily removed by rinsing. The marker incorporated in the complex is then quantitatively analysed. For quantitative analysis, any of the known methods may be used, including visual measurement, observations through various types of microscopes, measurement of absorbance of visual and ultraviolet rays, fluorophotometric measurement and pulse count measurement. In determination of the marker, other than the direct measurement of the marker labelled to the combined complex, a known quantity of the marker is used and the quantity of the marker which has not been conjugated to the complement component C1q may be determined to learn indirectly the quantity thereof introduced into the complex. Anyway, by the quantitative analysis of the marker, the quantity of the complement-binding antibody coupled to a specific antigen can be learned.

In the measurement or determination method of the invention, enzymes are particularly preferred as the signal emitting substance. Since enzymes act as catalysts, the sensitivities of the measurement may be freely adjusted by changing the temperature and time of the reaction.

Various antigens may also been inspected by the measurement method of the invention. The measurement of a variety of antigens may be utilized for the detection, identification, quantitative analysis and inspection of various substances including microorganisms such as chlamydia and virus, various physiologically active substances such as interferon and lymphokines, specific antigens for cancers, specific antigen substances in immunological abnormalities, allergens in allergic diseases, and medicinal substances such as hormones; and thus the method may be applied for various purposes, such as speedy and reliable diagnosis on a variety of diseases, provision of the standards for judging the effects of curing actions, inspection for doping, inspection for the determination of foreign matters in products, and hygienic or sanitary inspections.

When a specific antigen is measured by the method of the invention, a substance having affinity with the antigen which substance is fixed to a solid carrier is reacted with the antigen, and the complement component C1q labelled with a marker, and optinally with an antibody, followed by removal of unreacted materials and then the marker is quantitatively analyesd.

The substances having affinity with the antigen include various types of substances by which the antigens are readily absorbed, examples thereof being antibodies, portions of antibodies containing the sites binding to the antigens [for example, Fab, F(ab') or F(ab')$_2$], enzyme substrates and inhibitors, protein A of staphylococcus, various medicinal substances originated from organisms, and receptors for virus. A living tissue containing a substance having affinity with a specific antigen may be used without being purified. A selected one of these substances having affinities with antigens is fixed to the solid phase or carrier. By the use of the fixed phase, rinsing and other operations can be simplified. Any carriers may be used for this purpose, as far as the substances having affinities with antigens are not readily released or removed, and the same carrier materials as has been described for the method of measuring the complement-binding antibodies may be used.

A specific antigen to be measured is then added to the fixed substance having affinity with the antigen so that the antigen is conjugated with the substance. Any antigens may be measured by the method of the invention without particular limitation, as fas as they can be coupled with substances having affinities thereto, such as the corresponding antibodies. Illustative antigens which may be measured by the method of the invention include microorganisms such as viruses and bacteria, products produced by viruses and bacteria, vital components in animal tissues, physiologically active substances of plants, and chemicals. Sources for such antigens are body fluids such as blood, urine, cerebrospinal fluid and saliva, processed products of meats and plants, and aqueous solutions from rivers, sewege or waste water.

In the method of measuring an antigen, according to the invention, the corresponding antibody is added optionally as necessity arises. When an antibody or a portion of antibody having an antibody-binding activity and a complement-binding activity is used as the substance having the affinity with the antigen, it is not requisite to further add the antibody. However, in case where a susbstance having no complement-vinding activity is used as the substance having the affinity with the antigen, it is essential to add the antibody to be bound to the marker-labelled complement component C1q. The antibody may be added at any desired time point after the antigen is added, and may be added simultaneously with the addition of the complement component C1q or may be added before or after the addition of the complement component C1q. Of course, the antibody should be the one which binds uniquely to the specific antigen to be measured and should be capable of binding with the complement component C1q. Typical antibodies used commonly are immunoglobulins contained in animal blood sera, the examples being IgM, IgG etc. having complement-binding activities. Natural antibodies present in blood sera may be used, or desired antibodies may be obtained by administrating or infecting animals with antigens. In addition to the immunoglobulins purified and separated from blood sera, inactivated blood sera may be used as the antibodies without purification.

The condition for the reaction between the antigen, the substance having affinity with the antigen, and the marker-labelled complement component C1q and the antibody if it is added is not ristricted. Only by mixing the materials, the reaction proceeds spontaneously and quantitatively. While the time and temperature of the reaction vary depending on the specific kinds of the antigen and the other reactants, the reaction condition may be set with the only limitation that the biological activities of the reactants are preserved.

Since the comlex of the substance having affinity with the antigen, the antigen and the marker-labelled complement component C1q is fixed to the solid phase, the unreacted complement component C1q and inhibitors for the reaction may be easily removed by simple rinsing operation. The marker of the complex fixed to the solid phase is then quantitatively analysed. For the quantitative analysis, similar methods as has been described in determination of complement-binding antibody may be employed.

While in the above-mentioned methods for measurement a solid phase or carrier is employed, it is possible to measure without the use of such a solid phase or carrier. Specifically, after an antigen, an antibody and a marker-labelled complement component C1q are reacted, the marker may be measured directly without removing unreacted materials. In such a case, it is necessary to select a marker which is highly distinctive and is readily detectable. For example, if an enzyme such as peroxidase is used as a marker, the activity or sensitivity of the enzyme can be enhanced as the concentration of substrates is changed. Therefore, it is preferred to use enzyme as a marker. As another method in which a solid phase or carrier is not used, after an antigen, an antibody and a marker labelled-complement component C1q are reacted, a precipitating agent is added to precipitate unreacted materials such as unreacted complement component C1q and other unnecessary proteins followed by measuting the marker. The examples of the precipitating agent include materials which lower the solubility of proteins or agglutinate masses thereof, such as polyethyleneglycol, organic solvents such as ethanol, inorganic salts such as ammonium sulfate or sodium sulfate and organic or inorganic acids which change pH values of solutions such as trichloroacetic acid or hydrochloric acid. Basic materials may also be used to change the pH value. Ethylenediamine tetra-acetic acid or ethyleneglycol tetra-acetic acid may also be used as the precipitating agent since there compounds capture metal ions in the solutions, thereby lowering the solubility of proteins or agglutinate masses thereof.

Neutralizing antibodies may also be measured by the method of the invention. Neutralizing antibodies are antibodies for preventing infections by microorganisms, such as virus, rickettsia and chlamydia. Referring to diseases caused by virus, for instance, a wide variety of viral infectious diseases have been known up to date, including not a few serious diseases. For instance, if a pregnant woman is infected with rubella virus, there arises a danger that a malformed baby is born. Fatal damages are caused by the infection with rabies virus, Japanese encephalitis virus and poliovirus, with the nerval cells suffered unrecoverable disorders, leading to lasting troubles throughout the lifetime. Hepatitis caused by hepatitis virus is an infectious disease which lasts as a chronic disease for a very long time, and a portion of the liver is impaired by liver cirrhosis which might lead to hepatoma.

However, it is extremely hard to inhibit the growth of virus by the use of a variety of medicines including antibiotics, since a virus can grow in special living cells, i.e. the susceptible cells, unlike bacterium and fungi.

Accordingly, it is a more important counter-measure against the diseases caused by virus to prevent infection by virus or to protect a person from infection, apart from the curing treatement of the patients. The judgement on the question whether a person is susceptible to infection by a specific virus or not may be rendered by the determination of presence or absence of the neutralizing antibody to the virus under question and by the measurement of the titer of the existing neutralizing antibody.

A living body acquires sound immunity after it has been infected with a specific virus and then recovered from the disease caused thereby. This means, in fact, that a system for preventing the living body from reinfection with that virus has been established. In other words, a living body has been once infected with a specific virus, the antibody for protecting the body from re-infection is promoted, the antibody being referred to as infection preventing antibody. Production and preservation of the infection preventing antibody are very important factors against the infection by the virus. After being infected or immunized with a virus against the attack by the virus (for example inoculated by vaccine), various antibodies against the structural components of the virus have been produced in a living body. However, all of these antibodies produced in the living body are not participated in the prevention against infection by that virus. Only the antibody having the function for inhibiting the growth or propagation of the virus is referred to as neutralizing antibody or infection preventing antibody. This particular neutralizing antibody exerts the principal role in prevention of infection. The present invention provides a method of measuring a variety of neutralizing antibodies against all viruses, rickettsias and chlamydias which infect culture cells speedily and quantitatively on a number of samples.

In the method of measuring a neutralizing antibody, according to the invention, a liquid containing a known quantity of microorganism, such as virus, rickettsia or chlamydia, is reacted with a body fluid to be measured, such as blood, cerebrospinal fluid, saliva or blood serum. At this reaction step, the neutralizing antiboy, if present, reacts with the mixed microorganism. The amount of microorganism reacting with the neutralizing antibody is increased as the amount of neutralizing antibody contained in the liquid under measurement increases so that the amount of the residual microorganism is decreased. Since the content of microorganism in the measured liquid is known, the amount of neutralizing antibody contained in the measured liquid can be calculated from the result of determination of the residual microorganism.

After the preceding reaction step, the residual microorganism is inoculated on culture host cells to allow to grow. The cultivation is stopped after the lapse of preset time, whereby fixed cells containing therein the residual microorganism are obtained. A marker-labelled complement component C1q and an antibody against the microorganism are then added to react with the fixed cell to obtain a modified fixed cell to which the marker-labelled complement component C1q and the antibody are bound. By the quantitative analysis of the marker, the amount of residual microorganism can be learned to find the amount or titer of the neutralizing antibody.

The residual microorganism is, in general, cultivated initially by inoculating the microorganism on host cells cultivated through a monolayer culture on a micro plate to allow the microorganism to be absorbed by the micro plate, and then allowing it to grow or propagate on the plate. It is a common practice to inactivate endogenous enzymes and the microorganism by treating with, for example, methanol-containing hydrogen peroxide. Antibodies against the residual microorganism which may be used in the method include antisera, such as low titer human sera and animal immunoe sera, and monoclonal antibody.

Furthermore, the materials which may be measured by the method of the invention, other than those described above, are products produced or appearing internally of or on the surfaces of cells, and various microorganisms. The materials belonging to this category include cell surface antigens produced by cells, such as asialo $GM_1$, T antigen and Ly antigen; intracellular enzymes, such as TdT (terminal deoxynucleotidyl transferase), GTP ($\gamma$-glutamyl transpeptidase) and LDH (lactate dehydrogenase); secreting substances, such as CEA (carcino embryonic antigen) and AFP ($\alpha$-fetoprotein) and immunoglobulins: and enzymes and peptide base substances produced by yeasts and bacteria. The cells referred to above include all kinds of cells including animal cells, plant cells, heterokaryotes, cells of yeasts, bacteria and protozoa, and cells subjected to gene engineering. Microorganisms which may be measured by the method of the invention include all microorganisms infecting cultivated cells, such as viruses, rickettsias and chlamydias.

In measurement, one of the aforementioned substances or microorganisms is cultivated and fixed, or simply fixed, and then reacted with a complement-binding antibody and a marker-labelled complement component C1q, followed by determination of the marker, whereby the substance or microorganism may be quantitatively analysed.

EXAMPLES OF THE INVENTION

The invention will now be illustratively described with reference to examples thereof and comparative examples.

EXAMPLE 1

Enzyme-Conjugated Complement Component C1q:

(1) Purification 100 ml of a fresh rabbit blood serum was dialized through 5 l of a 0.026M aqueous solution of ethylene glycol tetra-acetate (pH 7.5) for 15 to 24 hours, and the formed precipitate was recovered by centrifugal separation (20,000G, 20 minutes). The recovered precipitate was dissolved in 20 ml of a 0.75M aqueous solution of sodium chloride (pH 5.0) containing 0.1M of sodium ethylenediamine tetra-acetate. After removing the insoluble materials by centrifugal separation (25,000G, 30 minutes), and then the solution was dialyzed through 5 l of 0.063M aqueous solution of sodium ethylenediamine tetra-acetate (pH 5.0) at 5° C. for 4 hours, followed by removal of precipitates by centrifugal separation (20,000G, 20 minutes). About 3 mg of proteins were obtained by the aforementioned operations, and 95% or more of the thus obtained proteins was occupied by the complement component C1q. In order to store the complement component C1q, the proteins were dissolved in an aqueous solution (pH 7.4) containing 0.05M tri(hydroxymethyl)aminomethane, 1M sodium chloride, 0.005M sodium ethylenediamine tetra-acetate and 10% sucrose. The aforementioned operations sequence may be repeated to further purify the complement component C1q.

(2) Preparation 30 mg of the thus purified rabbit complement component C1q was dissolved in 10 ml of an aqueous solution (pH 7.4) containing 0.05M tris(hydroxymethyl)aminomethane, 1M sodium chloride, 0.005M sodium ethylenediamine tetra-acetate and 10% sucrose. The solution was then added with 0.1 ml of a 0.1M dithiothreitol, and allowed to stand at room temperature for an hour for reaction. The reaction solution was then passed through a Sephadex G-25 (Trade Name of Pharmacia Fine Chemicals Co.) column to recover the protein fraction which was concentrated to have a volume of about 10 ml by ultrafiltration to obtain 22 mg of a reduced complement component C1q.

Separately, 20 mg of peroxidase extracted from the horseradish was dissolved in 6 ml of a phosphate buffer (pH 7.4), and then added with 4 ml of a dimethylformamide. The solution was further added with 0.2 ml of a 2% 4-(maleimidemethyl)-cyclohexane-1-carboxylic acid succineimide ester (hereinafter referred to as CHM) in dimethylformamide, and then allowed to stand at room temperature for an hour for reaction. After an hour, the solution containing the reaction product was passed through a Sephadex G-25 column to recover 16 mg of a CHM-conjugated peroxidase.

21 mg of the aforementioned reduced complement component C1q and 14 mg of the CHM-conjugated peroxidase were mixed together, and the mixture was allowed to stand stationarily at 4° C. to 10° C. for 15 hours and then passed through a Sepharose 6B (Trade Name of Pharmacia Fine Chemicals Co.) column to recover a fraction of a molecular weight range of from 400,000 to 800,000 to obtain 29 mg of a complement component C1q labelled with peroxidase.

EXAMPLE 2

Enzyme-conjugated Complement Component C1q 1 mg of β-D-galactosidase derived from Escherichia coli was dissolved in 0.2 ml of a 0.1M phosphate buffer (pH 6.0), and then reacted with 0.1 mg of N,N'-o-phenylenedimaleimide dissolved in 0.2ml of a phosphate buffer containing 5% dimethylformamide at 30° C. for 25 minutes. The solution containing the reaction product was passed through a Sephadex G-25 (Trade Name of Pharmacia Fine Chemicals Co.) column equilibrated with a phosphate buffer containing 0.2 mg/ml of bovine serum albumins, whereby a 720 μg of β-D-galactosidase coupled with maleimide.

200 μg of the β-D-galactosidase coupled with maleimide was dissolved in 0.1 ml of a phosphate buffer containing 1 mM of sodium ethylenediamine tetra-acetate, and reacted with 2 mg of the recuced complement component C1q prepared in Example 1 and dissolved in 0.1 ml of a phosphate buffer containing 1 mM of sodium ethylenediamine tetra-acetate at 4° C. for 48hours. The solution containing the reaction product was subjected to gel filtration using a Sepharose 6B (Trade Name of Pharmacia Fine Chemicals Co.) column, and then processed through the procedures as described in Example 1 to obtain an active fraction, i.e. a fraction containing 1.6 mg of a complement component C1q combined with β-D-galactosidase.

EXAMPLE 3

Enzyme-conjugated Complement Component C1q (1) Preparation

Generally following to the same procedures as in Example 1, except that a goat serum was used in place of the rabbit serum, a reduced complement component C1q was prepared, which was then conjugated with peroxidase to obtain a peroxidase-labelled complement component C1q.

(2) Test

Using a serum having a CF antibody titer of 16, the reactions of the thus obtained peroxidase-labelled complement component C1q with a herpes simplex virus CF antigen and with a normal cell antigen were inspected by means of the solid phase enzyme immunoassay to obtain the results as set forth in the following Table 1. In Table 1, the results of this Example are shown together with the results of the following Comparative Example 1.

COMPARATIVE EXAMPLE 1

Enzyme-conjugated Complement Component C1q Prepared by Conventional Process and Having the Enzyme Conjugated Generally at Random (1) Preparation 1.5 mg of horseradish peroxidase was dissolved in 0.2 ml of distilled water, and added with 60 μl of a 0.1M sodium periodate solution, followed by agitation at room temperature for 20 minutes. The solution was dialized through an acetate buffer (pH 4.4) containing 1M sodium chloride, added with 60 mg of sucrose, and then added with 1 ml of a carbonate buffer (pH 9.2) containing 3 mg of purified goat complement component C1q and also containing 1M sodium chloride and 10% of sucrose. After agitating for 2 hours, the mixture was further added with 0.1 ml of a 4 mg/ml solution of sodium borohydride, and then allowed to stand at 4° C. for additional 2 hours. Thereafter, the admixture was subjected to gel filtration through a Sephacryl S-300 (Trade Name of Pharmacia Fine Chemicals Co.) column, and the fraction having both of the peroxidase activity and the C1q activity was collected.

(2) Test

Using a serum having a CF antibody titer of 16, the reactions of the thus obtained peroxidase-labelled complement component C1q with a herpes simplex virus CF antigen and with a normal cell antigen were inspected by means of the solid phase enzyme immunoassay to obtain the results as set forth in the following Table 1. In Table 1, the results of this Comparative Example are shown while comparing with the results of Example 3.

TABLE 1

|  | Color Development of Herpes CF Antigen Well | Color Development of Normal Antigen Well |
| --- | --- | --- |
| Enzyme-Labelled C1q of Example 3 | 0.544 | 0.078 |
| Enzyme Labelled C1q of Comparative Example 1 | 0.328 | 0.281 |

It should be appreciated from the results shown in Table 1 that the enzyme-labelled complement component C1q prepared by the conventional process reacts with the normal antigen inselectively or non-uniquely and and has a low or feeble capability of reacting with the herpes simplex virus CF antigen selectively or uniquely; whereas the enzyme-labelled complement component C1q prepared by the process of the invention is considerably lowered in inselective or non-unique reaction with the normal antigen to have a sufficiently high capability of reaction with the herpes simplex virus CF antigen.

EXAMPLE 4

Toxin-Conjugated Complement Component C1q (1) Preparation

4mg of purified ricin A chain was disolved in 1.2 ml of a phosphate buffer (pH 7.0) containing 20% of dimethylformamide, and added with 30 μl of a phosphate buffer containing 3% of 4-(maleimidemethyl)cyclohexane-1-carboxylic acid succineimide ester (hereinafter referred to as CHM) to react at room temperature for an hour. Then, the solution containing the reaction product was passed through a Sephadex G-25 column to obtain 2.3 mg of a CHM-conjugated ricin which was dissolved in 1 ml of 0.1M phosphate buffer (pH 6.0) and then added with 2.5 mg of the reduced complement component C1q prepared by the same process as in Example 3 and dissolved in 0.5 ml of a phosphate buffer to react with the latter by allowing to stand the mixture at 4° C. for 22 hours. The reaction mixture was subjected to gel filtration using Sephacryl S-200 (Trade Name of Pharmacia Fine Chemicals Co.) to obtain 1.9 mg of a ricin-conjugated complement component C1q.

(2) Test

The T cell was refined from the BALB/c mouse spleen cell primed with DNP-KLH by passing the primed cell through a Nylon wool column. The T cell fraction was put into a RPMI-1640-10%FCS culture medium containing anti-mouse Ly-2,3 antiserum and 2 μg/ml of the aforementioned ricin-conjugated complement component C1q, and then allowed to stand stationarily at 37° C. for an hour. Thereafter, the processed cell was rinsed with a Hanks' balanced salt solution, cultivated in a RPMI-1640-10%FCS culture medium containing mouse Interleukin 2 for 7 days, and the distribution of the recovered cell Ly antigen was checked to find that the number of cells having the Ly-1 antigen on the surfaces thereof were increased as large as 1.6 times of those of a control which had not been processed with the anti-mouse Ly-2,3 antiserum and the ricin-conjugated complement component C1q.

EXAMPLE 5

Dyestuff-Conjugated Complement Component C1q (1) Preparation 10 mg of purified bovine serum albumin was dissolved in 1 ml of 0.5M carbonate buffer and added with 0.4 mg of fluorescein isothiocyanate (hereinafter referred to as FITC). After reacting the mixture for 7 hours, the reaction mixture was subjected to gel filtration to obtain bovine serum albumin combined with FITC. 8.2 mg of the bovine serum albumin combined with FITC was then dissolved in 0.4 ml of a 0.1M sodium phosphate buffer (pH 7.0), and added with 50 μl of a 90 mg/ml solution of CHM in dimethylformamide for reaction at 30° C. for an hour. After removing the insoluble materials by centrifugal separation, the buffer solution was exchanged to 0.1M phosphate buffer (pH 6.0). 0.56 ml of the solution was added with 0.5 ml of a 0.1M phosphate buffer (pH 6.0) containing 8 mg of the reduced complement component C1q prepared in Example 1 and 5 mM sodium ethylenediamine tetra-acetate, and the admixture was maintained at 4° C. for 18 hours. After then, the admixture was filtered through a gel filter of Sepharose 6B column to obtain 12 ml of an eluate fraction having a molecular weight ranging within 400,000 to 900,000 and containing a reaction product between the complement component C1q and the bovine serum albumin combined with the FITC.

(2) Test

Separately, the spleen cells were removed from the BDF₁ mouse and passed through a Nylon column to obtain T-cells. The thus obtained T-cells, a rabbit antiserum against mouse brain associated T-cell antigen and the eluate fraction prepared through the process desribed in the preceding paragraph were mixed together to form a mixture having a concentration of 150 times of the final concentration. After maintaining the mixture on ice for an hour and rinsing sufficiently, the cell was floated on the surface of a 50% glycerin-phosphate buffer solution and observed through a flourescent microscope. The result was that 93% of the cells emitted fluorescent light to reveal that almost all of the cells were the T-cells.

EXAMPLE 6

Complement-Component C1q Conjugated with Donor or Acceptor for Electron (1) Preparation Chlorophyllin a was dissolved in distilled water so that a 1 mg/ml solution was formed, and the pH value of the solution was adjusted with hydrochloric acid to pH 7.5, followed by addition of 1-ethyl-3-(3-dimethylaminopropyl)carbodiimide chloride and ethylenediamine so that the resultant reaction mixture contained 0.1M of the former and 0.8M of the latter. The mixture was allowed to stand for reaction for 120 minutes. The reaction product was purified by the use of CM-Sephadex (Trade Name of Pharmacia Fine Chemicals Co.), and 450 μg of aminoethylated chlorophyllin a was dissolved in 0.5 ml of a 0.1M phosphate buffer (pH 7.0) containing 40% of dimethylformamide. The solution of purified aminoethylated chlorophyllin a was mixed with 0.5 ml of a 40% dimethylformamide solution containing 2% of CHM, and maintained at 30° C. for an hour to react with CHM. The reaction mixture was subjected to gel filtration using Biogel P-2 (Trade Name of Bio-Rad Laboratories Inc.) to obtain CHM-chrolophyllin a. 12 ml of the reduced complement component C1q prepared in accordance with the process as described in Example 3 and 100 μg of the CHM-chrolophyllin a were put into 1.5 ml of a 0.1M phosphate buffer (pH 6.0), and allowed to stand stationarily at 4° C. for 18 hous, followed by gel filtration at which a fraction having a molecular weight ranging within 400,000 to 600,000 was picked up, whereby 7.5 mg of chrolophyllin-labelled complement component C1q was obtained.

(2) Test

Separately, a chemically modified antigen electrode was prepared by coating an antigen protein against herpes simplex virus on an $SnO_2$ Nesa electrode so that the antigen protein was combined with the electrode through a covalent bond. The electrode was immersed in a 25mM phosphate buffer (pH 6.95) containing 50 mM hydroquinone, a 1/50 final concentration of a human blood serum (CF =32) including an anti-herpes simplex virus, and 10 μg of the chrolophyllin-labelled complement component C1q, and irradiated by a white light while maintaining the electrode potential at 0.1 Vs·SCE, whereupon generation of photocurrents was observed. The quantum efficiencies of photocurrents were about 9%.

EXAMPLE 7

Magnetizable Substance-Conjugated Complement Component C1q (1) Preparation

Polystyrene microbeads each having amino groups at the surface thereof and containing micro grains of magnetite were suspended in 1 ml of 0.1M phosphate buffer (pH 7.0) containing 20% dimethylformamide, and added with 40 μl of 0.1M phosphate buffer containing 2.5% CHM, followed by moderate agitation at 30° C. for 60 minutes for reaction. After rinsing the beads, they were suspended again in 1 ml of 0.1M phosphate buffer (pH 6.0) and added with 0.5 ml of another phosphate buffer containing 1.8 mg of the reduced complement component C1q prepared by the process as described in Example 3, and then the admixture was allowed to react at 4° C. for 18 hours under moderate agitation. The beads were rinsed with a Veronal buffer solution (pH 7.4) containing 0.1% of gelatin, the solution being referred to as GVB hereinafter, and then stored in the GVB at 4° C.

(2) Test

Separately, the spleen cells of X5563 tumor-bearing C3H/He mouse were cultivated on a culture medium containing IL-2, and the once rinsed cells were again floated on the same culture medium and mixed with the beads-conjugated complement component C1q prepared by the process described in the preceding paragraph and an anti I-Jk antiserum, followed by stationary standing at 37° C. for 2 hours. After the lapse of the pre-set time, the cells were collected and then the collected cells were again floated gently, and an intense magnetical force was applied from the exterior of the container to capture the cells having the I-Jk antigens at the surfaces thereof. The cytotoxic activity of the cell left in the culture medium against the X5563 tumor cell was recognized to be about 1.4 times higher than that of the cell cultivated for 5 days in a simple IL-2.

EXAMPLE 8

Measurement of Complement-Binding Antibody

On a 96 well microtiter plate absorbing a complement-fixed antigen of the herpes simplex virus added, respectively, were 5 μl of each of sample sera inactivated to have complement-binding titers of less than 4 and 16, and then 95 μl of the peroxidase-labelled complement component C1q in Example 1 (diluted to 100 times volume with a gelatine-Veronal buffer solution) was added, followed by stationary standing at room temperature for an hour. Thereafter, each well was rinsed three times with a phosphate buffer containing 0.05% of Tween-20 (a surface active agent produced and sold by Nakarai Chemicals LTD.), and added with 100 μl of an $H_2O_2$-ABTS solution [2,2'-adino-di-(3-ethyl-benzothiazoline sulfate) solution containing hydrogen peroxide], followed by standing at room temperature for an hour to complete the reaction. After adding with 100 μl of an enzymatic reaction terminating agent, the light absorbance at 414 nm was measured to find that the absorbance of the serum having the complement-binding titer of less than 4 was 0.029 while that of the serum having the complement-binding titer of 16 was 0.579.

EXAMPLE 9

Measurement of Complement-binding Antibody

Bovine blood serum albumin was dissolved in a saline solution buffered by phosphate to prepare a solution having a concentration of 20 μg/ml, which was poured in each well of a 96 well microtiter plate and then maintained at room temperature for 2 hours to be absorbed by each well. After removing free bovine blood serum albumin, 50 μl of anti-bovine serum albumin rabbit antiserum (stepwisely diluted by 800 to 6400 times with a gelatin-Veronal buffer) and 50 μl of the β-D-galactosidase-labelled complement component C1q synthesized in Example 2 were added, and the microtiter plate was allowed to stand at room temperature for 30 minutes. After rinsing each well, 100 μl of o-nitrophenyl β-D-galactoside solution (in a phosphate buffer solution having a pH value of 7.3) was added, followed by standing at room temperature for 60 minutes, and then 0.1 ml of a 0.1M sodium carbonate solution to terminate or cease the enzymatic reaction. The light absorbances of respective wells were measured at a wavelength of 420 nm to find that the light absorbances were gradually varied from 0.421 to 0.063 depending on the change in dosed amounts of antiserum.

EXAMPLE 10

Measurement of Complement-binding Antibody

A purified antigen of herpes simplex virus was absorbed by 6.35 mm of polystyrne beads which were put into a small test tube, and added simultaneously with 0.1 ml of a 10 times diluted solution of a solution of each of inactivated test sera (having the complement-binding titers of 16 and less than 4) in a gelatine-Veronal buffer and with 0.1 ml of a solution of the peroxidase-labelled complement component C1q prepared in Example 1 diluted with the same buffer. The admixture was then allowed to stand stationarily at room temperature for an hour. After rinsing the beads, they were transferred to another small test tube, and added with 0.3 ml of an o-phenylenediamine solution to react at room temperature for 45 minutes. The reaction was terminated by the addition of 2 ml of 1 N hydrochloric acid, and the light absorbances of the samples at the wavelength of 490 nm were measured. The sample having the complement-binding titer of less than 4 had a light absorbance of 0.18, whereas the sample having the complement-binding titer of 16 had a light absorbance of 0.408.

EXAMPLE 11

Measurement of Antigen

A 96 well microtiter absorbing guinea pig anti-herpes simplex virus antibody (Fab) was supplied with 0.1 ml of uterus cervix swabs of a patient, and stationarily held at room temperature for 60 minutes. After rinsing the plate with the PBS (a 0.85% saline-containing phosphate buffer having a pH value of 7.4) for three times, each well was added with 0.05ml of either one of the inactivated guinea pig anti-herpes simplex virus sera (having the complement-binding antibody titers of 16 to 32) and also with 0.05ml of the peroxidase-labelled complement component C1q prepared in Example 1. The plate was held stationarily at room temperature for 60 minutes. Then, each well was rinsed with PBS containing 0.05% of Tween-20 (a surface active agent produced and sold under such Trade Name from Nakarai Chemicals LTD.), and added with 0.01 ml of $H_2O_2$-ABTS [2,2'-adino-di(3-ethyl-benzothiazolin sulfate) containing hydrogen peroxide]solution to be held at room temperature for an hour for reaction. Thereafter, 0.05 ml of a 0.05% aqueous sodium nitride which acted to terminate the enzymatic reaction, and then the light absorbances of respective sample wells at a wavelength of 414 nm were measured to find that the sample well filled with uterus cervix swabs of a patient who was negative against the herpes simplex virus had an absorbance of 0.030 and that the sample wells filled with uterus cervix swabs of a patient who were positive against the herpes simplex virus had absorbances of 0.113, 0.300, 0.550 and so on.

EXAMPLE 12

Measurement of Antigen

According to a conventional process, a lymphocyte fraction was prepared from the mouse spleen cell, followed by rinsing with the PBS, and then the concentration of the cell was adjusted to $1 \times 10^7$/ml. 0.1 ml of the thus prepared lymphocyte fraction, 0.05 ml of antimouse Thy-1,3 alloserum, and 0.05 ml of the FITC-labelled complement component C1q of Example 5 were mixed together and allowed to stand at room temperature for an hour. The cells were then rinsed thoroughly with the PBS and observed through a fluorescent microscope. The result revealed that 37% of the cells were fluorescent.

EXAMPLE 13

Measurement of Antigen

The lymphocytes in a blood of a leukemia patient were suspended in 1 ml of a phosphate buffer to prepare a suspension containing $1 \times 10^8$/ml of lymphocytes, and the suspension was processed by an ultra-sonicator for 2 minutes. The homogenate was then clarified by centrifugal separation, and the supernatant was added with 0.5ml of DNA Sepharose to react therewith at 37° C. for 60 minutes. The DNA Sepharose was bound with DNA related enzymes, such as DNA polymerase and terminal deoxynucleotidyl transferase (TdT). Then, 0.1 ml of the peroxidase-labelled complement component C1q and an inactivated rabbit anti-TdT serum, followed by reaction at 37° C. for 30 minutes. After rinsing thoroughly with PBS, the DNA Sepharose was recovered, to which 1 ml of a solution of $H_2O_2$-ABTS, was added, and the admixture was reacted at 37° C. for 60 minutes. Then, 1 ml of a 0.05% aqueous solution of sodium nitride acting as a terminator for the reaction, and the light absorbance of the supernatant was measured at a wavelength of 414 nm. It could be judged that the sample having a light absorbance value of not more than 0.075 showed that the patient was negative to TdT and that the sample having a light absorbance value of not less than 0.100 showed that the patient was positive to TdT and suffered from acute leukemia.

EXAMPLE 14

Measurement of Neutralizing Antibody

Two sample sera having, respectively, neutralizing antibody titers of 32 and 128 to the HSV (Herpes Simplex Virus) were diluted with a phosphate buffer to have the volumes four times as large as the initial volumes, heated at 56° C. for 30 minutes to be inactivated, and then further diluted with the same buffer to have egiht times volumes. 0.1 ml for each of the thus inactivated and diluted sample sera was mixed with 0.7 ml of the same buffer containing $4 \times 10^3$ pfu/ml of HSV, and then kept at 37° C. for 60 minutes to proceed the reaction.

Separately, Vero cells had been cultivated through the momolayer culture on a microplate, onto which a mixture of the serum and the HSV was added at a content of 50 μl/well, and then the virus was absorbed by holding the plate in a culture filled with 0.5% carbon dioxide and maintained at 37° C. for 60 minutes, with the addition of a maintenance medium followed by cultivation for additional 24 hours. Then, the cell was fixed by the use of methanol containing 3% of hydrogen peroxide.

After fixing by the methanol containing 3% of hydrogen peroxide, as described in the preceding paragraph, 50 μl for each of human sera having complement-fixing titers against the HSV diluted by 50 times with a gelatine-Veronal buffer (pH 7.4), respectively, of 16 and less than 4 was poured into individual wells, and then each well was added with 0.2 μg/50 μl/well of the peroxidase-labelled goat complement component C1q prepared in Example 3 and dissolved in the same buffer. After allowing to stand the microplate at room temperature for 2 hours, each well was rinsed with a phosphate buffer solution containing 0.05% of Tween 20 for three times, and then added with 0.7 ml/well of a $H_2O_2$-ABTS solution to develop coloring of each well which was subjected to light absorbance determination conducted at a wavelength of 414 nm. The results are shown in Table 2.

TABLE 2

| Serum for Detection of Residing Virus | OD414 | | (1)–(2) |
|---|---|---|---|
| Serum for Determination of Presence or Absence of | Well (1) Added with Guinea Pig | Well (2) Added with Normal | |
| Neutralizing Antibody | Anti-HSV Serum | Guinea Pig Serum | |
| Control (Well Not Added with Sample Serum) | 0.618 | 0.095 | 0.523 |
| Sample Serum Having Neutralizing Titer of 32 | 0.504 | 0.092 | 0.412 |
| Sample Serum Having Neutralizing Titer of 128 | 0.117 | 0.101 | 0.016 |

EXAMPLE 15

Measurement of Neutralizing Antibody

An anti-HSV positive human blood serum having a neutralizing antibody titer of 128 and a negative human blood serum were diluted by four times with a phosphate buffer, and inactivated, and then a serial dilution series diluted by 4 to 512 times was prepared each for the both sera on a microtiter plate provided with a number of wells each having a volume of 0.1 ml/well. Each well was filled with 0.1ml of a buffer containing $4 \times 10^3$ pfu/ml of HSV. The following procedures were the same as in Example 14 to measure or determine the $OD_{414}$. The results are plotted in the graph illustrated in FIG. 1 wherein the abscissa indicates the dilution rate of each serum and the ordinate indicate the $OD_{414}$. As shown, for the positive serum, the dilution rate giving the value as large as ½ of the maximum $OD_{414}$ corresponds to the neutralizing antibody titer of 128.

EXAMPLE 16

Measurement of Intracellular Substance or Microorganism

A specimen to be inspected was picked up from a defected portions of HSV infected patient (pendedum or labia), and suspended in 1 ml of culture medium solution containing an antibiotic. 0.1 ml of the suspension was inoculated to two wells of a microplate in which Vero cells had been preliminarily cultivated, and further cultivated at 37° C. for 22 hours.

After the completion of 22 hour cultivation, the cultivated cells were fixed with 3% hydrogen peroxide-methanol, and 50 μl of a human serum diluted by 25 times with a gelatine-Veronal buffer (pH 7.4), the serum having an anti-HSV complement binding titer (CF titer) of 32 or less than 4, was put into individual wells together with 50 μl of a solution in the same buffer containing 90 ng of the peroxidase-labelled complement component C1q prepared in Example 3. After reacting at room temperature for 2 hours, each well was rinsed with a phosphate buffer containing 0.05% of Tween 20 for three times, added with 0.1ml/well of a hydrogen peroxide-ABTS solution (pH 4) followed by standing for an hour to develop coloring, and then the reaction was terminated by the addition of 0.1 ml of a 0.01% sodium azide. Thereafter, the light absorbance of the reaction product in each well was measured. The well added with the human blood serum having a CF titer of 32 had a light absorbance of 0.263, whereas the well added with the serum having a CF titer of less than 4 had a light absorbance of 0.089. From those result, it could be confirmed that the HSV virion was present in the specimen inspected.

EXAMPLE 17

Measurement of Intracellular Substance or Microorganism

With the aim to cloning a cell producing carcino embryonic antigen, the cell T3M-4 producing CEA from pancreas tumor was diluted to the limit (i.e. to 1 cell/well), and then cultivated on a 96 well microplate for 16 days. After removing the culture medium solution, 0.1 ml of tripsin-sodium ethylenediamine tetra-acetate was put into each well to float the cells, and then two plates preliminarily filled with 0.2 ml/well of a fresh culture medium solution were replicated so that repricas containing 20 μl/well of floating cells were prepared. The culture medium solution in one of the repricas was thrown away, followed by fixation of the cells with 3%$H_2O_2$-methanol, and then added with 0.1 ml of a 1/400 time diluted rabbit anti-CEA antiserum diluted with GVB (gelatine-Veronal buffer) and 110 ng/0.1ml/well of the peroxidase-labelled complement component C1q. After reacting at room temperature for 2 hours and rinsing, coloring of the well was developed by the addition of a solution of the substrate of ABTS [diammonium (2,2-azi)-di{3-ethylbenzothiazolin sulfonic acid}]. The $OD_{414}$ of respective wells ranged within 0.127 to 0.386. The cell in the well showing the maximum $OD_{414}$ was picked up from the other reprica, and subjected to expansion.

EXAMPLE 18

Measurement of Intracellular Substance or Microorganism

100 μg (0.1 ml) of purified α-fetoprotein and 0.1 ml of Freund complete adjuvant were mixed together and dosed into the abdorminal cavity of a 7 week age Blb/C mouse. After 28 days from the dosage of the aforementioned materials, 100 μg (0.3 ml) of of AFP (α-fetoprotein) was additionally dosed, and after 3 days of the dosage of the AFP, the renal cells were picked up and fused with NS-1 cells. The cells were spread over a 96 well plate at a concentration or distribution density of $1 \times 10^5$/ml. From the first day to the sixteenth day after fusing, selection by the HAT medium (hypoxantine-thymidine-aminopterine medium) was conducted, and the antibody activity of the supernatant of each cultivated well was inspected on the seventeenth day to reveal that prodcution of antibody was recognized at a rate of 64/948 wells and production of anti-AFP antibody was recognized in two wells. The cells in respective wells were utilized as coated specimens while being processed by 3%$H_2O_2$-methanol to be fixed, and then added with 20 μl of a goat anti-mouse IgG (γ-chain selectivity) diluted by 200 times and also with 18 ng/20 μl of the peroxidase-labelled complement component C1q, followed by stational standing for 2 hours. After rinsing thoroughly, development of coloring of each cell was effected in a diaminobenzidine solution, and the number of cells producing the IgG was counted to find that the ratio of positive cells were 62% and 91%, respectively.

EXAMPLE 19

Measurement without Solid Carrier 0.5 ml of diluted solution of normal guinea pig serum, 0.5 ml of Herpes Simplex virus and 1 ml of the peroxidase-labelled complement component C1q solution prepared in Example 1, were charged into a small test tube, mixed together and reacted at 0° C. for 90 minutes. Alternatively, the same procedures were repeated except in that 0.5 ml diluted solution of guinea pig serum solution immunized three times with Herpes Simplex virus was used in place of 0.5 ml of diluted solution of normal guinea pig serum. Then, 1 ml of each of polyethyleneglycol solutions was added to each of the reaction products so that ultimate concentration reached 3%. After each of the resulting reaction products was allowed to stand at room temperature, precipitates were removed by centrifugal separation. Each of these precipitates was again dissolved in 2 ml of a buffer solution so as to be again processed with polyethyleneglycol. Finally, a 0.175% $H_2O_2$—0.04% ABTS solution (pH 4.0) was added to each of the thus processed solutions to develop the color and the OD 414 value was measured with a spectrophotometer. It was found that the OD 414 value for the immunized guinea pig serum was 1.025 while that for the normal serum was 0.092.

EXAMPLE 20

Conjugated Complement COmponents C1q 4 mg of the goat complement component C1q prepared in Example 3 was dissolved in a tris buffer solution (pH 7.5) and the resulting solution was reduced with dithiothreitol. The buffer solution was then replaced by gel filtration by a 0.1M solium phosphate buffer solution (pH 6.0) containing 5 mM of ethylenediamine tetra-acetate (EDTA), and the solution was then concentrated to 0.2 mM. The resulting solution was then admixed with 0.2 ml of the same buffer solution containing 0.1mg of N,N'-oxydimethylenedimaleimide and the resulting admixture was maintained at 4° C. for 22 hours. The unreacted materials were removed by gel filtration to produce 910 μg of conjugated complement components C1q.

EXAMPLE 21

Antibody-conjugated Complement Component C1q

2mg of immunoglobulin G to be specifically bound with sheep blood cells (anti-SRBC-IgG) was reacted with 150 μg of 4-maleimidemethyl)cyclohexane-1-carboxylic acid succineimide ester (CHM) in a phosphate buffer solution (pH 7.0). After gel filtration, the reaction product was concentrated to 0.2 ml. The resulting product was then reacted with 3 mg of the reduced complement component C1q dissolved in 0.2 ml of a phosphate buffer solution containing 2mM of ethylenediamine tetra-acetate (EDTA)(pH 7.0). After gel filtration, 520 μg of the complement component C1q conjugated with the anti-SRBC-IgG was obtained.

Upon adding the complement component C1q together with the SRBC to a liquid containing a blood serum antigen (BSA) and an anti-BSA antibody, agglutination of SRBC occurred to a more or less degree depending on the amount of the BSA antigen.

Although he present invention has been described with reference to the specific examples, it should be understood that various modifications and variations can be easily made by those skilled in the art without departing from the spirit of the invention. Accordingly, the foregoing disclosure should be interpreted as illustrative only and not to be interpreted in a limiting sense. The present invention is limited only by the scope of the following claims.

What is claimed is:

1. A complement component C1q wherein a substance is conjugated via a sulfur atom to at least one site of said component, said site not being involved in binding immunoglobulins, said substance being selected from the group consisting of signal emitting substances and cell function regulating substances, said signal emitting substance being a member selected from the group consisting of enzymes, coenzymes, enzyme substrates, dyestuffs and pigments, magnetizable substances, donors and acceptors for electron transference, radioactive substances, metal compounds, metal compositions and agglutinating substances, said cell function regulating substance being selected from the group consisting of antibiotics, growth factors, hormones, cell activation factors, cell division factors, anticancer agents and toxins.

2. The complement component C1q according to claim 1, wherein said enzyme is selected from the group consisting of peroxidases, alkaline phosphatases, galactosidases and alcohol dehydrogenases.

3. The complement component C1q according to claim 1, wherein said coenzyme is selected from the group consisting of nicotinamide adenine dinucleotide, nicotinamide adenine dinucleotide phosphate, flavin adenine dinucleotide and flavin adenine dinucleotide phosphate.

4. The complement component C1q according to claim 1, wherein said enzyme substrate is selected from the group consisting of o-nitrophenyl-β-D-galactopyranoside and 3-hydroxysteroid.

5. The complement component C1q according to claim 1, wherein said dyestuff and pigments are selected from the group consisting of hemoglobin, methylene blue and fluorescein isothiocyanate.

6. The complement component C1q according to claim 1, wherein said magnetizable susbstance is selected from the group consisting of carbonic iron, iron-containing microcapsules and complexes of iron with proteins.

7. The complement component C1q according to claim 1, wherein said donor and acceptor for electron transference are chlorophyl.

8. The complement component C1q according to claim 1, wherein said radioactive substance is selected from the group consisting of $^{124}$I-labelled albumin, p-chloro($^{203}$Hg)mercuribenzoic acid, N-ethyl(2,3-$^{14}$C)maleimide and iode(1-$^{14}$C)acetamide.

9. The complement component C1q according to claim 1, wherein said metal compound and said metal composition are selected from the group consisting of gold colloid and iron-containing microbeads.

10. The complement component C1q according to claim 1, wherein said antibiotic is selected from the group consisting of amphotericin B and actinomycin D.

11. The complement component C1q according to claim 1, wherein said growth factor is selected from the group consisting of selenium compounds, insulin, transferrin and epidermal growth factor.

12. The complement component C1q according to claim 1, wherein said hormone is corticosteroid.

13. The complement component C1q according to claim 1, wherein said cell activation factor is a macrophage activation factor.

14. The complement component C1q according to claim 1, wherein said cell division factor is a B cell division factor.

15. The complement component C1q according to claim 1, wherein said anticancer agent is mitomycin C.

16. The complement component C1q according to claim 1, wherein said toxin is ricin of toxin of castor bean.

17. The complement component C1q according to claim 1, wherein said agglutinating substance is selected from the group consisting of fine particles of latexes, fine particles of microbeads, a complement component C1q, a combination of an antibody and an antigen corresponding to said antibody, a combination of lectin and a material having saccharide structure corresponding to said lectin, a combination of biotin and avidin, and a combination of protein and IgM.

18. A process for preparing a substance-conjugated complement component C1q, comprising the steps of:
  (a) adding a reducing agent to a complement component C1q to cleave at least one S—S bond present at a site not involved in binding immunoglobulins thereby to obtain a reduced complement component C1q having at least one exposed —SH group; and
  (b) conjugating a substance to said complement component C1q via said exposed —SH group.

19. The process according to claim 18, wherein said reducing agent is a sulfur-containing compound.

20. The process according to claim 19, wherein said reducing agent is selected from the group consisting of mercaptoethylamine, dithiothreitol, 2-mercaptoethanol, cysteine and glutathione.

21. The process according to claim 18, wherein said reducing agent is allowed to act on the complement component C1q which is dissolved in a buffer solution for permitting the complement component C1q to be present stably.

22. The process according to claim 18, wherein said buffer solution is selected from the group consisting of tris buffered saline and phosphate buffered saline.

23. The process according to claim 18, wherein said reducing agent is allowed to act on said complement component C1q at −2° C. to 45° C. for 30 seconds to 24 hours.

24. The process according to claim 18, further comprising a step of removing excess reducing agent after the completion of said step (a).

25. The process according to claim 18, wherein said substance is selected from the group consisting of signal emitting substances and cell function regulating substances.

26. The process according to claim 18, wherein said substance is conjugated directly to said exposed —SH group.

27. The process according to claim 18, wherein said substance is conjugated to said exposed —SH group indirectly via a second susbstance having coupling function.

28. The process according to claim 18, wherein said second substance having said coupling function has a group selected from the group consisting of maleimide residue and —SH group, and also has a group for coupling said substance.

29. The process according to claim 18, wherein said substance is peroxidase extracted from horseradish, and wherein said second substance having said coupling function is N-hydroxysuccinimide ester of maleimide.

30. The process according to claim 18, wherein said substance is conjugated to said reduced complement component C1q in a buffer solution for both of said substance to be conjugated and said reduced complement component C1q.

31. The process according to claim 18 wherein said step (b) is a step of conjugating said substance indirectly via a second susbstance having coupling function and via said exposed —SH group to said complement component C1q, and wherein said step (b) is effected in a common buffer for said reduced complement component C1q, said second substance having coupling function and said substance to be conjugated.

* * * * *